United States Patent
Kwak et al.

(10) Patent No.: US 10,088,413 B2
(45) Date of Patent: Oct. 2, 2018

(54) SPECTRAL MATCHING BASED CALIBRATION

(71) Applicant: KLA-Tencor Corporation, Milpitas, CA (US)

(72) Inventors: Hidong Kwak, San Jose, CA (US); Zhiming Jiang, Pleasanton, CA (US); Ward RDell Dixon, Livermore, CA (US); Kenneth Edward James, Jr., Morgan Hill, CA (US); Leonid Poslavsky, Belmont, CA (US); Torsten Kaack, Los Altos, CA (US)

(73) Assignee: KLA-Tencor Corporation, Milpitas, CA (US)

(*) Notice: Subject to any disclaimer, the term of this patent is extended or adjusted under 35 U.S.C. 154(b) by 465 days.

(21) Appl. No.: 13/680,273

(22) Filed: Nov. 19, 2012

(65) Prior Publication Data

US 2013/0132021 A1 May 23, 2013

Related U.S. Application Data

(60) Provisional application No. 61/562,154, filed on Nov. 21, 2011.

(51) Int. Cl.
*G01N 21/27* (2006.01)
*G03F 7/20* (2006.01)
*G01N 21/21* (2006.01)

(52) U.S. Cl.
CPC ......... *G01N 21/274* (2013.01); *G01N 21/211* (2013.01); *G03F 7/70608* (2013.01)

(58) Field of Classification Search
CPC .... G01N 21/274; G01N 21/211; G01N 21/93; G03F 7/70608; G01B 11/06
See application file for complete search history.

(56) References Cited

U.S. PATENT DOCUMENTS 5,581,350 A 12/1996 Chen et al.
5,798,837 A * 8/1998 Aspnes et al. ............. 356/369
(Continued)

FOREIGN PATENT DOCUMENTS

KR 10-0956209 B1 5/2010
TW 200733287 9/2007
(Continued)

OTHER PUBLICATIONS

Collins, "Automatic rotating element ellipsometers: Calibration, operation, and real-time applications" Review of Scientific Instruments 61, 2029 (1990).*
(Continued)

*Primary Examiner* — John Kuan
(74) *Attorney, Agent, or Firm* — Spano Law Group; Joseph S. Spano (57) ABSTRACT

Methods and systems for calibrating system parameter values of a target inspection system are presented. Spectral Error Based Calibration (SEBC) increases consistency among inspection systems by minimizing differences in the spectral error among different inspection systems for a given specimen or set of specimens. The system parameter values are determined such that differences between a spectral error associated with a measurement of a specimen by the target inspection system and a spectral error associated with a measurement of the same specimen by a reference inspection system are minimized. In some examples, system parameter values are calibrated without modifying specimen parameters. Small inaccuracies in specimen parameter values have little effect on the calibration because the target system and the reference system both measure the same specimen or set of specimens. By performing SEBC over a set of specimens, the resulting calibration is robust to a wide range of specimens under test.

23 Claims, 4 Drawing Sheets

(56) References Cited

U.S. PATENT DOCUMENTS

| | | | | |
|---|---|---|---|---|
| 5,859,424 A * | 1/1999 | Norton | | G03F 7/70616 |
| | | | | 250/216 |
| 7,067,819 B2 * | 6/2006 | Janik | | G01J 3/10 |
| | | | | 250/252.1 |
| 7,075,649 B1 | 7/2006 | Johs et al. | | |
| 7,349,090 B2 * | 3/2008 | Wack | | G01N 21/211 |
| | | | | 356/369 |
| 7,359,052 B2 * | 4/2008 | Fielden | | G01J 3/10 |
| | | | | 356/369 |
| 7,436,527 B2 * | 10/2008 | Opsal | | G01B 11/0641 |
| | | | | 356/124 |
| 7,564,552 B2 * | 7/2009 | Fielden | | G03F 7/70916 |
| | | | | 356/364 |
| 7,612,891 B2 * | 11/2009 | Wan | | 356/503 |
| 2002/0109839 A1 | 8/2002 | Faus et al. | | |
| 2006/0138344 A1 | 6/2006 | Gunstream et al. | | |
| 2007/0219738 A1 | 9/2007 | Weiher et al. | | |
| 2007/0228287 A1 | 10/2007 | Ward et al. | | |
| 2008/0201095 A1 * | 8/2008 | Yip et al. | | 702/85 |
| 2009/0074137 A1 | 3/2009 | Agnihotri et al. | | |
| 2009/0103081 A1 | 4/2009 | Whelan et al. | | |
| 2009/0139312 A1 | 6/2009 | Hawthorne et al. | | |
| 2010/0231902 A1 | 9/2010 | Markwort et al. | | |
| 2010/0279213 A1 * | 11/2010 | Levy | | G01B 11/24 |
| | | | | 430/30 |
| 2011/0020956 A1 * | 1/2011 | Nemoto | | G01B 11/24 |
| | | | | 438/7 |
| 2011/0069312 A1 * | 3/2011 | Kandel | | G01N 21/956 |
| | | | | 356/369 |
| 2011/0114951 A1 * | 5/2011 | Kamikubo | | G01B 11/06 |
| | | | | 257/48 |
| 2011/0176133 A1 | 7/2011 | Dang et al. | | |
| 2011/0178785 A1 | 7/2011 | Tinnemans et al. | | |
| 2012/0257200 A1 * | 10/2012 | Blasenheim | | G02B 7/28 |
| | | | | 356/369 |

FOREIGN PATENT DOCUMENTS

| | | |
|---|---|---|
| TW | 200737269 | 10/2007 |
| TW | 200746336 | 12/2007 |
| TW | 200935538 | 8/2009 |
| TW | 200952102 A1 | 12/2009 |

OTHER PUBLICATIONS

International Search Report and Written Opinion dated Mar. 29, 2013, for PCT Application No. PCT/US2012/066131 filed on Nov. 20, 2012, by KLA-Tencor Corporation, 8 pages.

Supplementary European Search Report dated Sep. 21, 2015, for PCT Application No. PCT/US2012/066131 filed on Nov. 20, 2012, by KLA-Tencor Corporation, 3 pages.

* cited by examiner

| REFERENCE TOOL MEASURED THICKNESS (ANGSTROM) | TARGET TOOL MEASURED THICKNESS BEFORE SEBC (ANGSTROM) | | TARGET TOOL MEASURED THICKNESS AFTER SEBC (ANGSTROM) | |
|---|---|---|---|---|
| | THICKNESS | DIFF | THICKNESS | DIFF |
| 26.22622 | 25.18 | -1.04 | 26.47 | 0.24 |
| 26.8208 | 25.83 | -0.99 | 27.09 | 0.27 |
| 27.22362 | 26.20 | -1.02 | 27.44 | 0.21 |
| 26.16191 | 25.13 | -1.03 | 26.41 | 0.24 |
| 26.43895 | 25.44 | -1.00 | 26.73 | 0.29 |
| 27.16585 | 26.14 | -1.03 | 27.39 | 0.23 |
| 25.86422 | 24.87 | -1.00 | 26.13 | 0.27 |
| 26.92859 | 25.94 | -0.98 | 27.19 | 0.26 |
| 27.13468 | 26.11 | -1.03 | 27.32 | 0.18 |
| 26.21317 | 25.18 | -1.03 | 26.48 | 0.26 |
| 26.5922 | 25.60 | -0.99 | 26.87 | 0.27 |
| 27.12168 | 26.09 | -1.03 | 27.33 | 0.21 |

SPECTRAL MATCHING BASED CALIBRATION

CROSS REFERENCE TO RELATED APPLICATION

The present application for patent claims priority under 35 U.S.C. § 119 from U.S. provisional patent application Ser. No. 61/562,154, entitled "Spectral Matching Based Calibration," filed Nov. 21, 2011, the subject matter of which is incorporated herein by reference.

TECHNICAL FIELD

The described embodiments relate to systems for wafer inspection, and more particularly to characterization and defect detection of thin films used in semiconductor manufacturing.

BACKGROUND INFORMATION

Semiconductor devices such as logic and memory devices are typically fabricated by a sequence of processing steps applied to a substrate or wafer. The various features and multiple structural levels of the semiconductor devices are formed by these processing steps. For example, lithography among others is one semiconductor fabrication process that involves generating a pattern on a semiconductor wafer. Additional examples of semiconductor fabrication processes include, but are not limited to, chemical-mechanical polishing, etch, deposition, and ion implantation. Multiple semiconductor devices may be fabricated on a single semiconductor wafer and then separated into individual semiconductor devices.

Inspection processes are used at various steps during a semiconductor manufacturing process to detect defects on wafers to promote higher yield. As design rules and process windows continue to shrink in size, inspection systems are required to capture a wider range of physical defects on wafer surfaces while maintaining high throughput.

A variety of calibration procedures are performed on semiconductor inspection systems to ensure the measurement accuracy of a particular inspection system. In some examples, a reference wafer (or set of reference wafers) with known properties is measured by an inspection system. Parameters of the inspection system are tuned such that the measurement result generated by the inspection system matches the known characteristics of the reference wafer. This procedure ensures the measurement accuracy of the calibrated inspection system for wafers with properties that closely match those of the reference wafer.

In a manufacturing environment, measurement consistency across a fleet of inspection systems tasked with the same measurement objective is also important. If measurement consistency among inspection systems degrades, consistency among processed semiconductor wafers is lost and yield drops to unacceptable levels. To some extent measurement consistency may be obtained by calibrating each inspection system of a fleet of inspection systems with a reference wafer (or set of reference wafers). However, to obtain high accuracy results, calibration experiments involving the reference wafer must be performed in a carefully controlled environment that matches the environmental conditions in place when the reference wafer was originally characterized. This may be difficult to achieve in a manufacturing environment and lead to loss of consistency among inspection systems. In addition, an expensive reference wafer set must be maintained in the manufacturing environment. Risks of wafer breakage or degradation potentially jeopardize the integrity of the calibration process. Moreover, the accuracy of an inspection system calibrated based on reference wafers is typically limited to wafers with properties that closely match those of the reference wafer.

Accordingly, it would be advantageous to develop improved calibration methods for inspection systems to ensure measurement consistency over a wide range of wafers and across a fleet of inspection systems.

SUMMARY

Methods and systems for calibrating system parameter values of a target inspection system are presented. The embodiments described herein generally relate to methods for increasing measurement consistency among inspection systems by minimizing the differences in the spectral error among different inspection systems for a given specimen or set of specimens. System parameter values of a target inspection system are calibrated such that the difference between a spectral error associated with a measurement of a specimen by the target inspection system and a spectral error associated with a measurement of the same specimen by a reference inspection system is minimized.

Spectral Error Based Calibration (SEBC) increases consistency among inspection systems by minimizing the differences in the spectral error among different inspection systems for a given specimen or set of specimens. System parameters being calibrated are tuned such that the resulting spectral error is close to that of the reference inspection system without modifying specimen parameters. By performing SEBC over a set of specimens with a wide range of specimen parameter values, the resulting calibration is robust to a wide range of specimens under test. Also, by matching spectral errors between inspection systems rather than measured spectra, inspection systems with different nominal system parameter values may be calibrated to deliver consistent measurement results.

In one example, an indication of a measured spectral response of a specimen by a target inspection system 100 is received by a computing system 116. A spectral error associated with the target inspection system 100 is determined by computing system 116. The spectral error is based on differences between the measured spectral response of the specimen and a modeled spectral response of the specimen by the target inspection system. The modeled spectral response includes at least one system parameter and at least one specimen parameter. An indication of a spectral error associated with a reference inspection system is also received by the computing system 116. The spectral error is based on differences between a measured spectral response of the same specimen measured by the target inspection system and a modeled spectral response of the specimen by the reference inspection system. The value of at least one system parameter of the target inspection system is determined by computing system 116. The value (or values) is determined such that an error function that includes a difference between the spectral error of the target inspection system and the spectral error of the reference inspection system is minimized.

The terms reference inspection system and target inspection system generally refer to an inspection scenario (e.g., the target inspection system) that requires adaptation of the system parameters to obtain measurement consistency with another inspection scenario (e.g., the reference inspection system). In this manner, the target is being calibrated with respect to the reference.

In some examples, the target inspection system and the reference inspection system are different tools. In some other examples, SEBC may be performed periodically on an individual inspection system to maintain measurement stability over time. Over time the physical characteristics of a particular inspection system may drift. The inspection system may be recalibrated to compensate for drift over time by running SEBC periodically. In this scenario, the reference inspection system is the inspection system in a physical state at a relatively early time when a particular wafer is inspected. The target inspection system is the same inspection system in a changed physical state (e.g., after drift has occurred) at a later time when the same wafer is inspected again. In yet another example, SEBC may be performed before and after any preventative maintenance operation is performed on a particular inspection system. In this manner, SEBC is performed to recalibrate the system to recover the measurement performance of the system before preventative maintenance was performed. In yet another example, SEBC may be performed as a diagnostic of the health of an inspection system. If the spectral error match degrades, it may be an indication that the hardware of the inspection system is compromised and must be repaired to return to active service.

The foregoing is a summary and thus contains, by necessity, simplifications, generalizations, and omissions of detail. Consequently, those skilled in the art will appreciate that the summary is illustrative only and is not limiting in any way. Other aspects, inventive features, and advantages of the devices and/or processes described herein will become apparent in the non-limiting detailed description set forth herein.

DETAILED DESCRIPTION

Reference will now be made in detail to background examples and some embodiments of the invention, examples of which are illustrated in the accompanying drawings.

Figure 1:
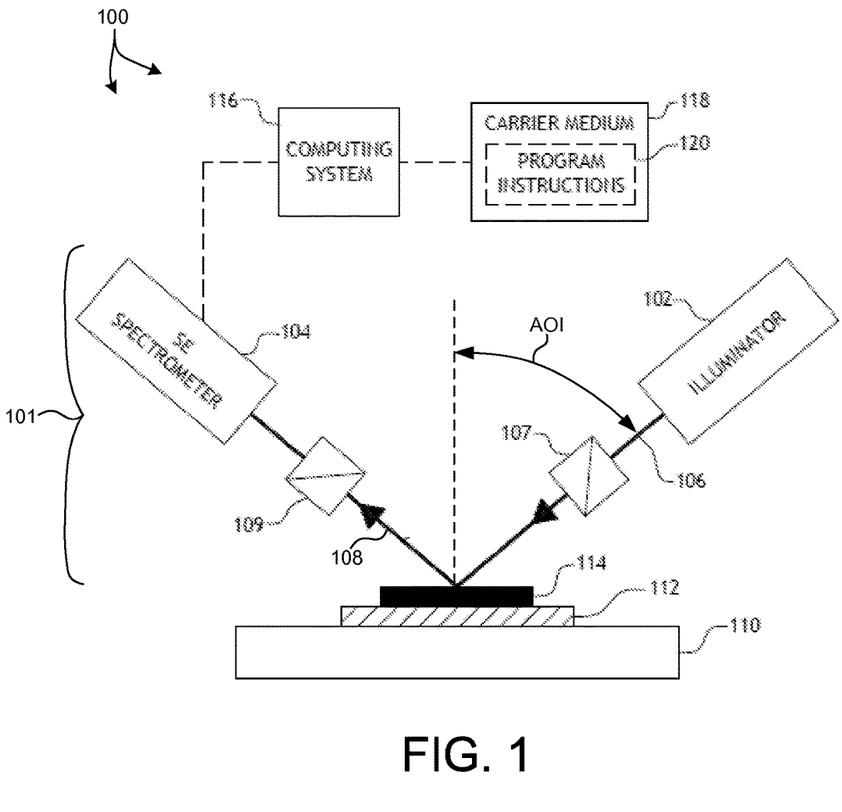
FIG. 1 is a simplified diagram illustrative of an inspection system 100 operable in accordance with the Spectral Error Based Calibration (SEBC) methods described herein.

FIG. 1 illustrates a system 100 for measuring characteristics of a thin film of a semiconductor wafer in accordance with the exemplary methods presented herein. As shown in FIG. 1, the system 100 may be used to perform spectroscopic ellipsometry on one or more films 114 of a semiconductor wafer 112 disposed on a wafer positioning system 110. In this aspect, the system 100 may include a spectroscopic ellipsometer equipped with an illuminator 102 and a spectrometer 104. The illuminator 102 of the system 100 is configured to generate and direct illumination of a selected wavelength range (e.g., 150-850 nm) to the thin film (e.g., HfSiON thin film) disposed on the surface of the semiconductor wafer 112. In turn, the spectrometer 104 is configured to receive illumination reflected from the surface of the semiconductor wafer 112. It is further noted that the light emerging from the illuminator 102 is polarized using polarizer 107 to produce a polarized illumination beam 106. The radiation reflected by the thin film 114 disposed on the wafer 112 is passed through an analyzer 109 and to the spectrometer 104. In this regard, the radiation received by the spectrometer 104 in the collection beam 108 is analyzed, allowing for spectral analysis of the thin film 114.

In a further embodiment, the inspection system 100 is a target inspection system 100 that may include one or more computing systems 116 employed to perform Spectral Error Based Calibration (SEBC) of the target inspection system 100. The one or more computing systems 116 may be communicatively coupled to the spectrometer 104. In one aspect, the one or more computing systems 116 are configured to receive the results of the one or more sampling processes from the spectrometer. The results include an indication of the measured spectral response of the specimen by target inspection system 100.

The one or more computing systems 116 determine a spectral error associated with the target inspection system 100. In this regard, the computing system 116 determines the spectral error as a difference between the measured spectra and a modeled spectral response of the specimen.

In addition, the one or more computing systems 116 are further configured to receive a spectral error associated with a reference inspection system. In some examples, the spectral error associated with the reference inspection system is stored in carrier medium 118 and retrieved by computing system 116. The spectral error associated with the reference inspection system is based on a difference between a measured spectral response and a modeled spectral response of the same specimen.

The one or more computer systems are further configured to determine a value of at least one system parameter of the inspection system 100 such that an error function that includes a difference between the spectral error of the target inspection system 100 and the reference inspection system is minimized. In this respect, a regression process (e.g., ordinary least squares regression) may be employed to identify system parameters of the inspection system that minimize differences between the spectral error associated with the reference inspection system and the spectral error of the inspection system.

Applicant notes that specifics related spectral error based calibration will be discussed in greater detail further herein.

Figure 2:
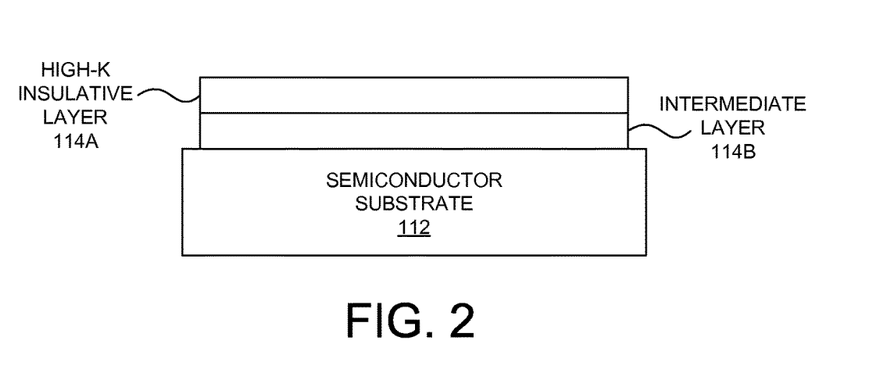
FIG. 2 is a simplified diagram illustrative of a semiconductor substrate 112 with attached thin film layers 114A and 114B.

As illustrated in FIG. 2, in some embodiments, a number of layers may be disposed on a semiconductor substrate 112. For example, an intermediate layer 114B is located between a semiconductor substrate 112 (e.g., silicon) and a high-k insulative layer 114A to promote adhesion between the high-k material and the semiconductor substrate. Typically, the intermediate layer 114B is very thin (e.g., ten Angstroms).

It should be recognized that the various steps described throughout the present disclosure may be carried out by a single computer system 116 or, alternatively, a multiple computer system 116. Moreover, different subsystems of the system 100, such as the spectroscopic ellipsometer 101, may include a computer system suitable for carrying out at least a portion of the steps described above. Therefore, the above description should not be interpreted as a limitation on the present invention but merely an illustration. Further, the one or more computing systems 116 may be configured to perform any other step(s) of any of the method embodiments described herein.

In another embodiment, the computer system 116 may be communicatively coupled to the spectrometer 104 or the illuminator subsystem 102 of the ellipsometer 101 in any manner known in the art. For example, the one or more computing systems 116 may be coupled to a computing system of the spectrometer 104 of the ellipsometer 101 and a computing system of the illuminator subsystem 102. In another example, the spectrometer 104 and the illuminator 102 may be controlled by a single computer system. In this manner, the computer system 116 of the system 100 may be coupled to a single ellipsometer computer system.

The computer system 116 of the system 100 may be configured to receive and/or acquire data or information from the subsystems of the system (e.g., spectrometer 104, illuminator 102, and the like) by a transmission medium that may include wireline and/or wireless portions. In this manner, the transmission medium may serve as a data link between the computer system 116 and other subsystems of the system 100. Further, the computing system 116 may be configured to receive spectral results via a storage medium (i.e., memory). For instance, the spectral results obtained using a spectrometer of an ellipsometer may be stored in a permanent or semi-permanent memory device. In this regard, the spectral results may be imported from an external system.

Moreover, the computer system 116 may send data to external systems via a transmission medium. Moreover, the computer system 116 of the system 100 may be configured to receive and/or acquire data or information from other systems (e.g., inspection results from an inspection system or metrology results from a metrology system) by a transmission medium that may include wireline and/or wireless portions. In this manner, the transmission medium may serve as a data link between the computer system 116 and other subsystems of the system 100. Moreover, the computer system 116 may send data to external systems via a transmission medium.

The computing system 116 may include, but is not limited to, a personal computer system, mainframe computer system, workstation, image computer, parallel processor, or any other device known in the art. In general, the term "computing system" may be broadly defined to encompass any device having one or more processors, which execute instructions from a memory medium.

Program instructions 120 implementing methods such as those described herein may be transmitted over or stored on carrier medium 118. The carrier medium may be a transmission medium such as a wire, cable, or wireless transmission link. The carrier medium may also include a computer-readable medium such as a read-only memory, a random access memory, a magnetic or optical disk, or a magnetic tape.

The embodiments of the system 100 illustrated in FIG. 1 may be further configured as described herein. In addition, the system 100 may be configured to perform any other block(s) of any of the method embodiment(s) described herein.

As illustrated in FIG. 1, a beam of broadband radiation from illuminator 102 is linearly polarized in polarizer 107, and the linearly polarized beam is then incident on specimen 112. After reflection from specimen 112, the beam propagates toward analyzer 109 with a changed polarization state. In some examples, the reflected beam has elliptical polarization. The reflected beam propagates through analyzer 109 into spectrometer 104. In spectrometer 104, the beam components having different wavelengths are refracted in different directions to different detectors. The detectors may be a linear array of photodiodes, with each photodiode measuring radiation in a different wavelength range.

In one example, computing system 116 receives the measured data from each detector, and is programmed with software for processing the data it receives in an appropriate manner. The measured spectral response of a specimen may be determined by analyzing the changes in polarization of radiation reflected from the sample in response to incident radiation having known polarization state in any number of ways known in the art.

Any of polarizer 107 and analyzer 109 may be configured to rotate about their optical axis during a measurement operation. In some examples, computing system 116 is programmed to generate control signals to control the angular orientation of polarizer 107 and/or analyzer 109, or other elements of the system 100 (e.g., wafer positioning system 110 upon which specimen 112 rests). Computing system 116 may also receive data indicative of the angular orientation of analyzer 109 from an analyzer position sensor associated with analyzer 109. Similarly, computing system 116 may also receive data indicative of the angular orientation of polarizer 107 from a polarizer position sensor associated with polarizer 107. Computing system 116 may be programmed with software for processing such orientation data in an appropriate manner.

In one embodiment, polarizer 107 is controlled so that it rotates at a constant speed. The signal received at each detector of spectrometer 104 will be a time-varying intensity given by:

$$I(t)=I_0[1+\alpha \cos(2\omega t-P_0)+\beta \sin(2\omega t-P_0)] \quad (1)$$

where $I_0$ is a constant that depends on the intensity of radiation emitted by illuminator 102, $\omega$ is the angular velocity of polarizer 107, $P_0$ is the angle between the optical axis of polarizer 107 and the plane of incidence (e.g., the plane of FIG. 1) at an initial time (t=0), and $\alpha$ and $\beta$ are values defined as follows:

$$\alpha=[\tan^2 \Psi-\tan^2(A-A_0)]/[\tan^2 \Psi+\tan^2 (A-A_0)] \quad (2)$$

and $$\beta=[2(\tan \Psi)(\cos \Delta)(\tan(A-A_0))]/[\tan^2 \Psi+\tan^2 (A-A_0)] \quad (3)$$

where $\tan(\Psi)$ is the amplitude of the complex ratio of the p and s components of the reflectivity of the sample and $\Delta$ is the phase of the complex ratio of the p and s components of the reflectivity of the sample. The "p" component denotes the component of polarized radiation whose electrical field is in the plane of FIG. 1, and "s" denotes the component of polarized radiation whose electrical field is perpendicular to the plane of FIG. 1. A is the nominal analyzer angle (e.g., a measured value of the orientation angle supplied, for example, from the above-mentioned analyzer position sensor associated with analyzer 109). $A_0$ is the offset of the actual orientation angle of analyzer 109 from the reading "A" (e.g., due to mechanical misalignment, $A_0$ may be non-zero).

From equations (1)-(3), values of $\alpha$ and $\beta$ may be determined based on a measurement of a particular specimen by inspection system 100. Hence, for a particular specimen, values $\alpha_{meas}$ and $\beta_{meas}$ are determined based on spectrometer data.

In general, ellipsometry is an indirect method of measuring physical properties of the specimen under inspection. In most cases, the measured values (e.g., $\alpha_{meas}$ and $\beta_{meas}$) cannot be used to directly determine the physical properties of the specimen. To resolve this problem, a model is created that attempts to predict the measured values (e.g., $\alpha_{meas}$ and $\beta_{meas}$). As illustrated in equations (4) and (5), the model includes parameters associated with the system ($P_{sys}$) and the specimen ($P_{specimen}$).

$$\alpha_{model}=f(P_{sys},P_{specimen}) \quad (4)$$

$$\beta_{model}=g(P_{sys},P_{specimen}) \quad (5)$$

System parameters are parameters used to characterize the inspection tool (e.g., ellipsometer 101). Exemplary system parameters include angle of incidence (AOI), analyzer angle ($A_0$), polarizer angle ($P_0$), illumination wavelength, numerical aperture (NA), etc. Specimen parameters are parameters used to characterize the specimen (e.g., specimen 112 including layers 114). Exemplary specimen parameters include refractive index, dielectric function tensor, nominal layer thickness of all layers, layer sequence, etc. The physical properties of a specimen under inspection are determined by an iterative procedure (e.g., regression). The unknown specimen parameters are varied and the model output values (e.g., $\alpha_{model}$ and $\beta_{model}$) are calculated until a set of specimen parameter values are determined that results in a close match between the model output values and the experimentally measured values (e.g., $\alpha_{meas}$ and $\beta_{meas}$). The remaining spectral mismatch between the modeled response and the experimentally captured response of the specimen under test is a spectral error. For spectral response values $\alpha$ and $\beta$, the respective spectral errors, $\delta\alpha$ and $\delta\alpha$ are expressed in equations (6) and (7).

$$\delta\alpha=\alpha_{meas}-\alpha_{model} \quad (6)$$

$$\delta\beta=\beta_{meas}-\beta_{model} \quad (7)$$

In one aspect, system parameter values of a target inspection system are calibrated such that differences between a spectral error associated with a measurement of a specimen by the target inspection system and a spectral error associated with a measurement of the same specimen by a reference inspection system are minimized. Spectral Error Based Calibration (SEBC) increases consistency among inspection systems by minimizing the differences in the spectral error among different inspection systems for a given specimen or set of specimens. System parameters being calibrated are tuned such that the resulting spectral error is close to that of the reference inspection system without modifying specimen parameters. Small inaccuracies in specimen parameter values have little effect on the calibration because the target system and the reference system both measure the same specimen or set of specimens. In addition, by performing SEBC over a set of specimens with a wide range of specimen parameter values, the resulting calibration is robust to a wide range of specimens under test. Also, by matching spectral errors between inspection systems rather than measured spectra, inspection systems with different system parameter values may be calibrated to deliver consistent measurement results. For example, an inspection system with an angle of incidence of sixty five degrees may be calibrated to deliver measurement results that are consistent with an inspection system with an angle of incidence of seventy degrees.

Figure 5:
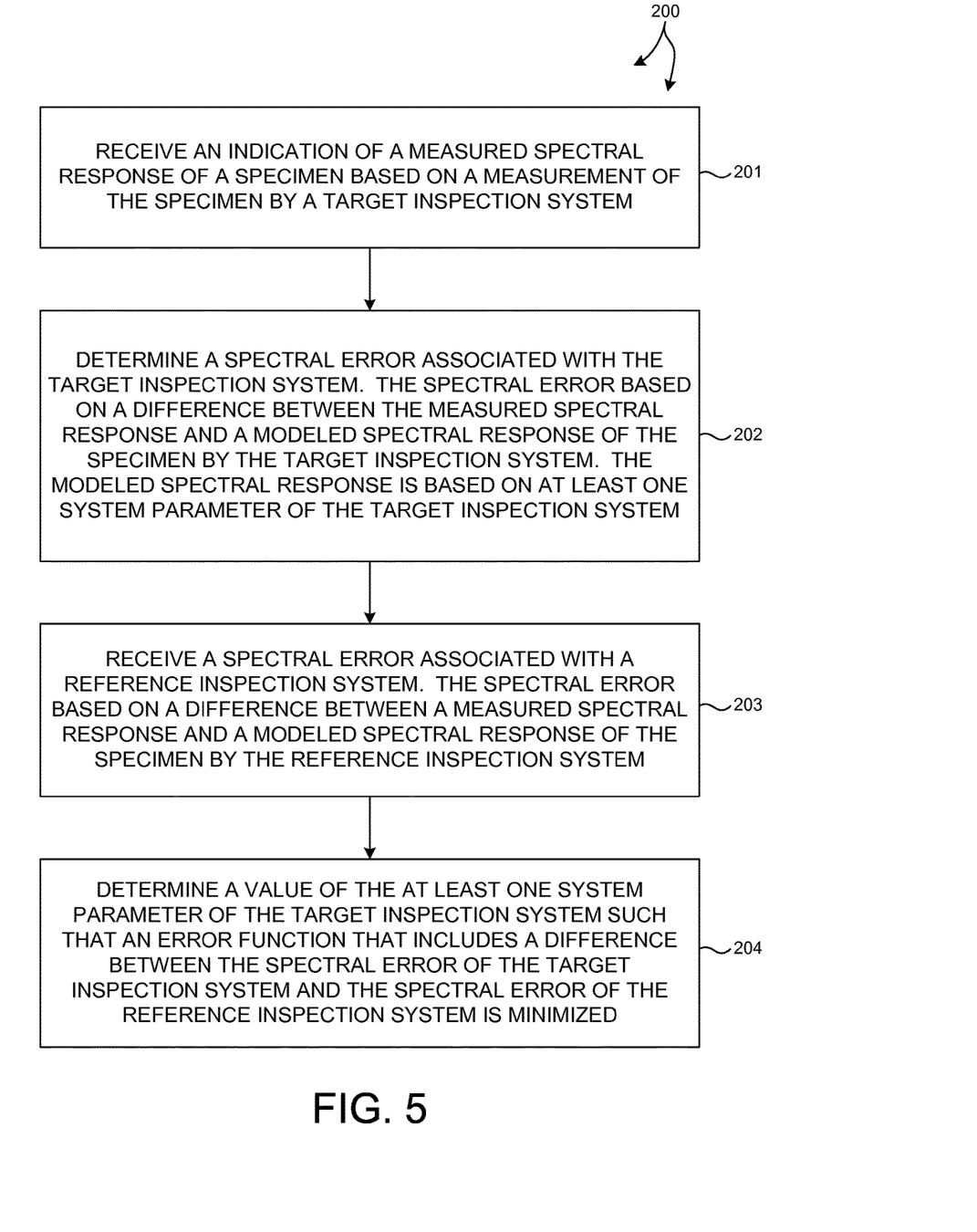
FIG. 5 is a flowchart illustrative of a method 200 of calibrating system parameters of an inspection system to minimize the differences in spectral error between at target inspection system and a reference inspection system.

FIG. 5 illustrates a method 200 suitable for implementation by the inspection system 100 of the present invention. In one aspect, it is recognized that data processing blocks of method 200 may be carried out via a pre-programmed algorithm executed by one or more processors of computing system 116. While the following description is presented in the context of inspection system 100, it is recognized herein that the particular structural aspects of inspection system 100 do not represent limitations and should be interpreted as illustrative only.

In block 201, an indication of a measured spectral response of a specimen by a target inspection system is received by computing system 116. For example, spectra may be received from a spectroscopic ellipsometer 101. In another example, spectra may be received from a reflectometer (not shown). The spectral data may be acquired from each of the thin films 114 deposited on the wafer 112 utilizing the spectroscopic ellipsometer 101. For instance, the spectroscopic ellipsometer 101 may include an illuminator 102 and a spectrometer 104, as discussed previously herein. The spectrometer 104 may transmit results associated with a spectroscopic measurement of the thin films of the wafer to one or more computing systems 116 for analysis. In another example, the spectra for multiple thin films 114 may be acquired by importing previously obtained spectral data. In this regard, there is no requirement that the spectral acquisition and the subsequent analysis of the spectral data need be contemporaneous or performed in spatial proximity. For instance, spectral data may be stored in memory for analysis at a later time. In another instance, spectral results may be obtained and transmitted to a computing system located at a remote location for analysis.

In one example, the indications of the measured spectral response are $\alpha_{meas}$ and $\beta_{meas}$ values derived from measurement data by methods known in the art as discussed hereinbefore with reference to equations (1)-(3). In other examples, other indications of the measured spectral response may be contemplated (e.g., tan $\Psi$ and $\Delta$, etc.). The aforementioned spectral response indications are provided by way of non-limiting example. Other indications or combinations of indications may be contemplated. It is important to note that a spectral indication is based on the spectral response of the specimen, not specific metrics (e.g., film thickness, index of refraction, dielectric constants, etc.) that may be derived from the spectral response of the specimen.

In block 202, a spectral error associated with the target inspection system 100 is determined by computing system 116. The spectral error is based on the difference between the measured spectral response of the specimen and a modeled spectral response of the specimen by the target inspection system. The modeled spectral response includes at least one system parameter and at least one specimen parameter as discussed hereinbefore with reference to equations (4)-(5).

In block 203, an indication of a spectral error associated with a reference inspection system is received by the computing system 116. The spectral error is based on a difference between a measured spectral response of the same specimen measured by the target inspection system and a modeled spectral response of the specimen by the reference inspection system. For example, the spectral error may be received by importing previously obtained spectral error data. In this regard, there is no requirement that the spectral acquisition and the subsequent analysis of the spectral data need be contemporaneous or performed in spatial proximity. For instance, spectral data may be stored in memory for analysis at a later time. In another instance, spectral results may be obtained and transmitted to a computing system located at a remote location for analysis.

In some examples, the spectral error associated with the reference inspection system may be determined by the computing system 116. In some examples, computing system 116 receives the measured spectral response of the specimen by the reference inspection system and the modeled spectral response of the specimen by the reference inspection system and determines the difference.

In block 204, the value of at least one system parameter of the target inspection system is determined by computing system 116. The value or values are determined such that an error function that includes a difference between the spectral error of the target inspection system and the spectral error of the reference inspection system is minimized.

In one example, a regression is performed to solve for the system parameter set ($P_{sys}$) of the target inspection system such that the error function, E, illustrated in equation (8), is minimized.

$$E = \sum_{i=1}^{N} [(\delta\alpha_{T,i}(P_{sys}) - \delta\alpha_{R,i})^2 + ((\delta\beta_{T,i}(P_{sys}) - \delta\beta_{R,i})^2)] \quad (8)$$

Error function, E, is a least squared error function that includes the sum of the squares of each of the differences between the spectral error of the target inspection system (e.g., $\delta\alpha_T$ and $\delta\beta_T$) and the reference inspection system (e.g., $\delta\alpha_R$ and $\delta\beta_R$) over each of the captured pixels (N pixels) for both $\alpha$ and $\beta$.

The error function presented in equation (8) is provided by way of example. Many other error functions may be employed to drive the regression of the system parameter values. For example, the error function may be weighted by uncertainty in $\alpha$ and $\beta$. In another example, the error function may be the minimization of the maximum value of the difference between the error spectra associated with the reference inspection system and the target inspection system. Other examples may be contemplated based on methods of parameter fitting that are known in the art.

The terms reference inspection system and target inspection system generally refer to an inspection scenario (e.g., the target inspection system) that requires adaptation of the system parameters to obtain measurement consistency with another inspection scenario (e.g., the reference inspection system). In this manner, the target is being calibrated with respect to the reference.

In some examples, the target inspection system and the reference inspection system are different tools. For example, in a manufacturing context, it may be advantageous to have a fleet of inspection systems each calibrated by SEBC with respect to a single reference inspection system. In this manner, each of the fleet of inspection systems is consistent with a single reference tool.

Figure 3:
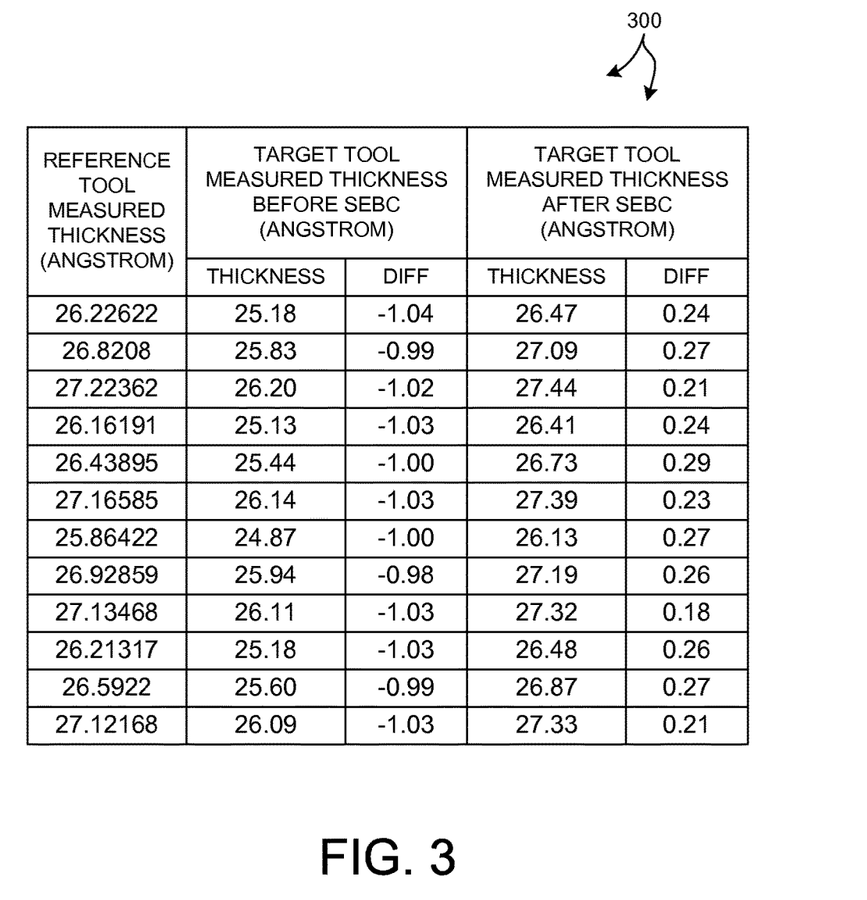
FIG. 3 illustrates a chart 300 indicative of an improvement in measurement consistency between two different inspection systems by implementing SEBC.

FIG. 3 illustrates a chart 300 indicative of an improvement in measurement consistency between two different inspection systems by implementing SEBC. As illustrated in FIG. 3, the first column shows a series of layer thickness measurements performed by a reference inspection system. The second column illustrates the results of the same series of thickness measurements on the same wafer by a target inspection system without performing SEBC. The difference between the two measurements is illustrated in the third column. The fourth column illustrates the results of the same series of thickness measurements on the same wafer by the target inspection system after performing SEBC as described herein. The differences between the thickness measurements by the target inspection system after calibration and the reference inspection system are illustrated in the fifth column. As illustrated by the smaller differences in fifth column, the measurement consistency between the target inspection system and the reference inspection system is significantly improved by implementing SEBC.

In some examples, SEBC may be performed periodically on an individual inspection system to maintain measurement stability over time. For example, over time the physical characteristics of a particular inspection system may drift. By running SEBC periodically, the inspection system may be recalibrated to compensate for drift over time. In this scenario, the reference inspection system is the inspection system in a physical state at a time when a particular wafer was inspected. The target inspection system is the same inspection system in a changed physical state (e.g., after drift has occurred) at a later time when the same wafer is inspected again. In this manner, SEBC may be performed to recalibrate the system parameters of the inspection system to ensure that the measurement behavior is consistent with measurement behavior of the same tool at an earlier time (e.g., when the tool was initially calibrated.).

In another example, SEBC may be performed before and after any preventative maintenance operation is performed on a particular inspection system. Periodically, an inspection system must be partially disassembled to perform preventative maintenance. When the inspection system is reassembled, the physical characteristics of the system are changed. SEBC may be performed to recalibrate the system to recover the measurement performance of the system before preventative maintenance was performed. In this manner, the reference inspection system is the inspection system in a physical state before the preventative maintenance operation and the target inspection system is the inspection system in a changed physical state after preventative maintenance.

Figure 4:
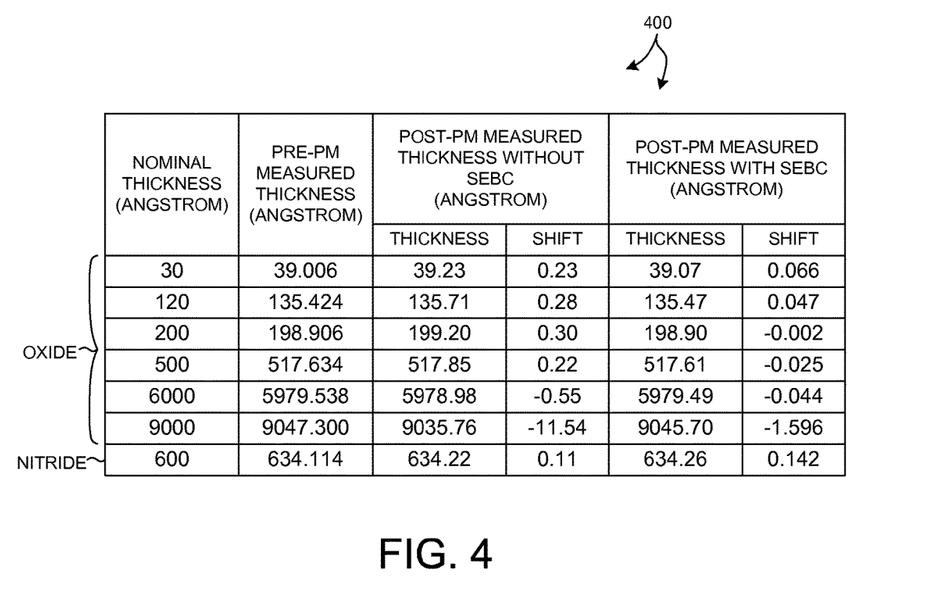
FIG. 4 illustrates a chart 400 indicative of an improvement in measurement consistency before and after a preventative maintenance operation by implementing SEBC as described herein.

FIG. 4 illustrates a chart 400 indicative of an improvement in measurement consistency before and after a preventative maintenance operation by implementing SEBC as described herein. As illustrated in FIG. 4, a number of different wafers, each having different oxide layer thicknesses, are measured by an inspection system before a preventative maintenance operation is performed. The nominal thickness of the oxide layer of each wafer is illustrated in the first column and the measurement results are illustrated in the second column. The third column shows the measurement results after the preventative maintenance operation and initial calibration by traditional techniques, but without performing SEBC. The shift in measurement results is illustrated in the fourth column. The shifts illustrate the limitations of traditional calibration techniques. The fifth column illustrates the measurement results after the preventative maintenance operation and calibration with SEBC. The sixth column illustrates the resulting shift in measurement results. As illustrated in this example, SEBC increases the measurement consistency before and after a preventative maintenance operation. Furthermore, system recovery time is reduced (by minimizing the need to engage in additional calibration operations), and in some cases, maintains the system baseline and correlations without additional calibration effort.

Furthermore, FIG. 4 illustrates an improvement in measurement consistency over a range of physical characteristics of a specimen. As illustrated in FIG. 4, different wafers, each having a different nominal oxide layer thickness, are measured by the inspection system. The nominal oxide layer thickness of each wafer is illustrated in the first column. An improvement in measurement consistency is demonstrated for a number of different wafers, each having a different oxide layer thickness. Measurement results for wafers with a large range of oxide layer thickness (30 Angstroms to 9000 Angstroms) are illustrated. Measurement consistency for each of oxide layer thicknesses is significantly improved by implementing SEBC as described herein.

In another example, SEBC may be performed as a diagnostic of the health of an inspection system. If the spectral error match degrades, it may be an indication that the hardware of the inspection system is compromised and must be repaired to return to active service.

The embodiments described herein generally relate to methods for increasing consistency among inspection systems by minimizing the differences in the spectral error among different inspection systems for a given specimen or set of specimens. System parameter values of a target inspection system are calibrated such that the difference between a spectral error associated with a measurement of a specimen by the target inspection system and a spectral error associated with a measurement of the same specimen by a reference inspection system is minimized. For example, one embodiment relates to a computer-implemented method for minimizing the differences in the spectral error among different inspection systems for a given specimen or set of specimens based on spectroscopic ellipsometer data. However, the methods described herein are not limited in the types of inspection systems from which spectral error may be derived. For example, in one embodiment, the inspection system includes a reflectometer for thin film inspection of the wafer.

As described herein, SEBC may be applied to one or more inspection systems in addition to other calibration methods. In some examples, each inspection system may be individually calibrated using known techniques and then SEBC may be applied to increase consistency among a group of inspection systems.

As described herein, the term "inspection system" includes any system employed at least in part to characterize a specimen in any aspect. Exemplary terms used in the art may include a "defect inspection" system or a "metrology" system. However, such terms of art do not limit the scope of the term "inspection system" as described herein. In addition, the inspection system 100 may be configured for inspection of patterned wafers and/or unpatterned wafers. The inspection system may be configured as a LED inspection tool, edge inspection tool, backside inspection tool, macro-inspection tool, or multi-mode inspection tool (involving data from one or more platforms simultaneously), and any other metrology or inspection tool that benefits from the calibration of system parameters based on differences in error spectra between a reference and a target inspection tool.

Various embodiments are described herein for a semiconductor processing system (e.g., an inspection system or a lithography system) that may be used for processing a specimen. The term "specimen" is used herein to refer to a wafer, a reticle, or any other sample that may be processed (e.g., printed or inspected for defects) by means known in the art.

As used herein, the term "wafer" generally refers to substrates formed of a semiconductor or non-semiconductor material. Examples include, but are not limited to, monocrystalline silicon, gallium arsenide, and indium phosphide. Such substrates may be commonly found and/or processed in semiconductor fabrication facilities. In some cases, a wafer may include only the substrate (i.e., bare wafer). Alternatively, a wafer may include one or more layers of different materials formed upon a substrate.

One or more layers may be formed upon a wafer. For example, such layers may include, but are not limited to, a resist, a dielectric material, a conductive material, and a semiconductive material. Many different types of such layers are known in the art, and the term wafer as used herein is intended to encompass a wafer on which all types of such layers may be formed.

One or more layers formed on a wafer may be "patterned" or "unpatterned." For example, a wafer may include a plurality of dies having repeatable pattern features. Formation and processing of such layers of material may ultimately result in completed devices. Many different types of devices may be formed on a wafer, and the term wafer as used herein is intended to encompass a wafer on which any type of device known in the art is being fabricated.

A typical semiconductor process includes wafer processing by lot. As used herein a "lot" is a group of wafers (e.g., group of 25 wafers) which are processed together. Each wafer in the lot is comprised of many exposure fields from lithography processing tools (e.g. steppers, scanners, etc.). Within each field may exist multiple die. A die is the functional unit which eventually becomes a single chip. One or more layers formed on a wafer may be patterned or unpatterned. For example, a wafer may include a plurality of dies, each having repeatable patterned features. Formation and processing of such layers of material may ultimately result in completed devices. Many different types of devices may be formed on a wafer, and the term wafer as used herein is intended to encompass a wafer on which any type of device known in the art is being fabricated.

A "reticle" may be a reticle at any stage of a reticle fabrication process, or a completed reticle that may or may not be released for use in a semiconductor fabrication facility. A reticle, or a "mask," is generally defined as a substantially transparent substrate having substantially opaque regions formed thereon and configured in a pattern. The substrate may include, for example, a glass material such as quartz. A reticle may be disposed above a resist-covered wafer during an exposure step of a lithography process such that the pattern on the reticle may be transferred to the resist.

In one or more exemplary embodiments, the functions described may be implemented in hardware, software, firmware, or any combination thereof. If implemented in software, the functions may be stored on or transmitted over as one or more instructions or code on a computer-readable medium. Computer-readable media includes both computer storage media and communication media including any medium that facilitates transfer of a computer program from one place to another. A storage media may be any available media that can be accessed by a general purpose or special purpose computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code means in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and blu-ray disc where disks usually reproduce data magnetically, while discs reproduce data optically with lasers. Combinations of the above should also be included within the scope of computer-readable media.

Although certain specific embodiments are described above for instructional purposes, the teachings of this patent document have general applicability and are not limited to the specific embodiments described above. Accordingly, various modifications, adaptations, and combinations of various features of the described embodiments can be practiced without departing from the scope of the invention as set forth in the claims.

What is claimed is:

1. A method comprising:
    providing a first amount of illumination light having wavelengths within a spectral band between 150 nanometers and 850 nanometers to one or more structures disposed on a semiconductor wafer;
    polarizing the first amount of illumination light before incidence on the semiconductor wafer;
    analyzing a first amount of light collected from the one or more structures disposed on the semiconductor wafer in response to the first amount of polarized illumination light provided to the semiconductor wafer;
    detecting the first amount of analyzed light with a spectrometer;
    generating a measured spectral response of the one or more structures as measured by a target inspection system from the first amount of detected light;
    estimating a modeled spectral response of the one or more structures as measured by the target inspection system based on a model of the spectral response of the one or more structures disposed on the semiconductor wafer as measured by the target inspection system, wherein the modeled spectral response is based at least in part on a value of at least one system parameter of the target inspection system;
    determining a first spectral error associated with the target inspection system based on a difference between the measured spectral response of the one or more structures and the modeled spectral response of the one or more structures as measured by the target inspection system;
    providing a second amount of broadband illumination light to the one or more structures disposed on the semiconductor wafer;
    detecting a second amount of light from a portion of the semiconductor wafer in response to the second amount of illumination light provided to the semiconductor wafer;
    generating a measured spectral response of the one or more structures as measured by a reference inspection system from the second amount of detected light, wherein a value of the at least one system parameter of the reference inspection system is different from the value of the at least one system parameter of the target inspection system;
    estimating a modeled spectral response of the one or more structures as measured by the reference inspection system based on a model of the spectral response of the one or more structures disposed on the semiconductor wafer as measured by the reference inspection system;
    determining a first spectral error associated with the reference inspection system based on a difference between the measured spectral response of the one or more structures and the modeled spectral response of the one or more structures as measured by the reference inspection system;
    determining an updated value of the at least one system parameter of the target inspection system such that an error function that includes a difference between the first spectral error of the target inspection system and the first spectral error of the reference inspection system is minimized;
    estimating a second modeled spectral response of the one or more structures as measured by the target inspection system based on the model of the spectral response of the one or more structures disposed on the semiconductor wafer as measured by the target inspection system, wherein the second modeled spectral response is based at least in part on the updated value of the at least one system parameter of the target inspection system; and
    determining a value of a parameter indicative of a structural property of the one or more structures such that an error function that includes a difference between the measured spectral response of the one or more structures as measured by the target inspection system and the second modeled spectral response is minimized.

2. The method of claim 1, wherein the target inspection system and the reference inspection system are spectroscopic ellipsometers.

3. The method of claim 1, wherein the reference inspection system is an inspection system in a first physical configuration and the target inspection system is the inspection system in a second physical configuration.

4. The method of claim 1, wherein the reference inspection system is an inspection system measured at a first time and the target inspection system is the inspection system measured at a second time after the first time.

5. The method of claim 1, wherein the at least one system parameter does not include a parameter associated with the one or more structures disposed on the semiconductor wafer.

6. The method of claim 1, wherein the value of the system parameter of the reference inspection system includes a nominal angle of incidence that is different from a nominal angle of incidence of the target inspection system.

7. The method of claim 1, further comprising:
    receiving an indication of a measured spectral response of one or more structures disposed on a second semiconductor wafer based on a measurement of the second semiconductor wafer by the target inspection system;
    determining a second spectral error associated with the target inspection system based on a difference between the measured spectral response of the second semiconductor wafer and a modeled spectral response of the second semiconductor wafer to the measurement by the target inspection system, the modeled spectral response of the second semiconductor wafer based at least in part on the at least one system parameter of the target inspection system;
    receiving a second spectral error associated with the reference inspection system based on a difference between a measured spectral response and a modeled spectral response of the second semiconductor wafer to a measurement of the second semiconductor wafer by the reference inspection system, and wherein the determining of the updated value of the at least one system parameter of the target inspection system involves minimizing an error function that includes the first and second spectral errors of the target inspection system and the first and second spectral errors of the reference inspection system.

8. The method of claim 1, wherein the at least one system parameter of the reference inspection system and the target inspection system is any of an angle of incidence, an analyzer angle, a polarizer angle, and a numerical aperture.

9. An inspection system comprising:
an illuminator configured to provide an amount of illumination light to one or more structures disposed on a semiconductor wafer;
a polarizer configured to polarize the amount of illumination light before incidence on the semiconductor wafer;
an analyzer configured to analyze an amount of light collected from the one or more structures disposed on the semiconductor wafer in response to the polarized illumination light provided to the semiconductor wafer;
a spectrometer configured to detect the amount of analyzed light and generate a measured spectral response of the one or more structures as measured by the inspection system from the amount of detected light; and
a non-transitory, computer-readable medium, comprising:
code for causing a computer to estimate a modeled spectral response of the measurement of the one or more structures disposed on the semiconductor wafer by the inspection system, wherein the modeled spectral response is based at least in part on a value of at least one system parameter of the inspection system;
code for causing the computer to determine a first spectral error associated with the inspection system based on a difference between the measured spectral response of the one or more structures disposed on the semiconductor wafer and a modeled spectral response of the one or more structures disposed on the semiconductor wafer by the inspection system;
code for causing the computer to receive a first spectral error associated with a reference inspection system based on a difference between a measured spectral response and a modeled spectral response of the one or more structures disposed on the semiconductor wafer by the reference inspection system, wherein a value of the at least one system parameter of the reference inspection system is different from the value of the at least one system parameter of the inspection system; and
code for causing the computer to determine an updated value of the at least one system parameter of the inspection system such that an error function that includes a difference between the first spectral error of the inspection system and the first spectral error of the reference inspection system is minimized;
code for causing the computer to estimate a second modeled spectral response of the measurement of the one or more structures disposed on the semiconductor wafer by the inspection system, wherein the second modeled spectral response is based at least in part on the updated value of the at least one system parameter of the inspection system; and
code for causing the computer to determine a value of a parameter indicative of a structural property of the one or more structures such that an error function that includes a difference between the measured spectral response of the one or more structures as measured by the inspection system and the second modeled spectral response is minimized.

10. The inspection system of claim 9, wherein the inspection system and the reference inspection system are spectroscopic ellipsometers.

11. The inspection system of claim 9, wherein the reference inspection system is the inspection system in a different physical configuration.

12. The inspection system of claim 9, wherein the reference inspection system is the inspection system measured at an earlier time.

13. The inspection system of claim 9, wherein the at least one system parameter does not include a parameter associated with the one or more structures disposed on the semiconductor wafer.

14. The inspection system of claim 9, wherein the value of the system parameter of the reference inspection system includes a nominal angle of incidence that is different from a nominal angle of incidence of the inspection system.

15. The inspection system of claim 9, wherein the non-transitory, computer-readable medium, further comprises:
code for causing the computer to receive an indication of a measured spectral response of one or more structures disposed on a second semiconductor wafer based on a measurement of the second semiconductor wafer by the inspection system;
code for causing the computer to determine a second spectral error associated with the inspection system based on a difference between the measured spectral response of the second semiconductor wafer and a modeled spectral response of the second semiconductor wafer to the measurement by the inspection system, the modeled spectral response of the second semiconductor wafer based at least in part on the at least one system parameter of the inspection system; and
code for causing the computer to receive a second spectral error associated with the reference inspection system based on a difference between a measured spectral response and a modeled spectral response of the second semiconductor wafer to a measurement of the second semiconductor wafer by the reference inspection system, and wherein the determining of the updated value of the at least one system parameter of the inspection system involves minimizing an error function that includes the first and second spectral errors of the inspection system and the first and second spectral errors of the reference inspection system.

16. The inspection system of claim 9, wherein the at least one system parameter is any of an angle of incidence, an analyzer angle, a polarizer angle, and a numerical aperture.

17. An inspection system comprising:
an illuminator configured to provide an amount of illumination light to one or more structures disposed on a semiconductor wafer;
a polarizer configured to polarize the amount of illumination light before incidence on the semiconductor wafer;
an analyzer configured to analyze an amount of light collected from the one or more structures disposed on the semiconductor wafer in response to the polarized illumination light provided to the semiconductor wafer;
a spectrometer configured to detect the amount of analyzed light, and generate a measured spectral response of the one or more structures as measured by the inspection system from the amount of detected light; and one or more computer systems configured to:
  estimate a modeled spectral response of the measurement of the one or more structures disposed on the semiconductor wafer by the inspection system, wherein the modeled spectral response is based at least in part on a value of at least one system parameter of the inspection system;
  determine a first spectral error associated with the inspection system based on a difference between the measured spectral response of the one or more structures disposed on the semiconductor wafer and a modeled spectral response of the one or more structures disposed on the semiconductor wafer by the inspection system;
  receive a first spectral error associated with a reference inspection system based on a difference between a measured spectral response and a modeled spectral response of the one or more structures disposed on the semiconductor wafer by the reference inspection system, wherein the reference inspection system includes a value of the at least one system parameter that is different from the value of the at least one system parameter of the inspection system;
  determine an updated value of the at least one system parameter of the inspection system such that an error function that includes a difference between the first spectral error of the inspection system and the first spectral error of the reference inspection system is minimized;
  estimate a second modeled spectral response of the measurement of the one or more structures disposed on the semiconductor wafer by the inspection system, wherein the second modeled spectral response is based at least in part on the updated value of the at least one system parameter of the inspection system; and
  determine a value of a parameter indicative of a structural property of the one or more structures such that an error function that includes a difference between the measured spectral response of the one or more structures as measured by the inspection system and the second modeled spectral response is minimized.

18. The inspection system of claim 17, wherein the reference inspection system is the inspection system in a different physical configuration.

19. The inspection system of claim 17, wherein the reference inspection system is the inspection system measured at an earlier time.

20. The inspection system of claim 17, wherein the at least one system parameter does not include a parameter associated with the one or more structures disposed on the semiconductor wafer.

21. The inspection system of claim 17, wherein the value of the at least one system parameter of the reference inspection system includes a nominal angle of incidence that is different from a nominal angle of incidence of the inspection system.

22. The inspection system of claim 17, wherein the one or more computer systems is further configured to:
  receive an indication of a measured spectral response of one or more structures disposed on a second semiconductor wafer based on a measurement of the second semiconductor wafer by the inspection system;
  determine a second spectral error associated with the inspection system based on a difference between the measured spectral response of the second semiconductor wafer and a modeled spectral response of the second semiconductor wafer to the measurement by the inspection system, the modeled spectral response of the second semiconductor wafer based at least in part on the at least one system parameter of the inspection system; and
  receive a second spectral error associated with the reference inspection system based on a difference between a measured spectral response and a modeled spectral response of the second semiconductor wafer to a measurement of the second semiconductor wafer by the reference inspection system, and wherein the determining of the updated value of the at least one system parameter of the inspection system involves minimizing an error function that includes the first and second spectral errors of the inspection system and the first and second spectral errors of the reference inspection system.

23. The inspection system of claim 17, wherein the at least one system parameter is any of an angle of incidence, an analyzer angle, a polarizer angle, and a numerical aperture.

* * * * *